United States Patent
Sellmann

(10) Patent No.: US 7,300,280 B2
(45) Date of Patent: Nov. 27, 2007

(54) DENTAL DEVICE FOR RECORDING THE POSITION OF THE JAWS OF A PATIENT IN RELATION TO ONE ANOTHER BY MEANS OF RECORDING PLATES

(75) Inventor: Hans Sellmann, Marl (DE)

(73) Assignee: Dentalgerate "Condylator", Peter T. Gerber (CH)

( * ) Notice: Subject to any disclaimer, the term of this patent is extended or adjusted under 35 U.S.C. 154(b) by 0 days.

(21) Appl. No.: 10/549,030

(22) PCT Filed: Feb. 9, 2004

(86) PCT No.: PCT/CH2004/000073

§ 371 (c)(1), (2), (4) Date: Jan. 9, 2006

(87) PCT Pub. No.: WO2004/082516

PCT Pub. Date: Sep. 30, 2004

(65) Prior Publication Data

US 2006/0127839 A1 Jun. 15, 2006

(30) Foreign Application Priority Data

Mar. 18, 2003 (CH) .................................... 0434/03

(51) Int. Cl.
*A61C 19/04* (2006.01)
(52) U.S. Cl. ...................................................... 433/68
(58) Field of Classification Search .................. 433/69, 433/68, 72
See application file for complete search history.

(56) References Cited

U.S. PATENT DOCUMENTS

| 2,447,287 A | 8/1948 | Smith et al. |
| 2,481,203 A | 9/1949 | Davies et al. |
| 2,876,541 A * | 3/1959 | Jensen ........................... 433/69 |
| 2,994,957 A * | 8/1961 | McLeod ....................... 433/69 |
| 3,564,717 A | 2/1971 | Ennor |
| 5,044,950 A | 9/1991 | Hobish et al. |
| 5,059,120 A | 10/1991 | Lee |
| 5,722,828 A * | 3/1998 | Halstrom ...................... 433/69 |

FOREIGN PATENT DOCUMENTS

DE 101 54 994 A1 9/2002

* cited by examiner

*Primary Examiner*—Melba Bumgarner
(74) *Attorney, Agent, or Firm*—George Pappas

(57) ABSTRACT

The invention comprises a pair of one-piece, flat recording plates that are mirror symmetric about a sagittal plane S, or which an upper part (200), which is provided with a stylus (202), can be affixed to the upper jaw of the patient, and a lower part (100), which is provided with a writing surface (101), can be affixed to the lower jaw of the patient. A recording plate comprises a planar base area (110; 210), planar transition areas (113, 114; 213, 214), which border thereon, and supporting surfaces (111, 112; 211, 212), which border on the latter and which have continuous retention openings (119; 219). The base area is approximately shaped in the form of a forward tapering isosceles trapezoid, which is mirror symmetric about the sagittal plane S, whereas each transition area is approximately shaped in the form of an elongated parallelogram, which is angled away both from the base area as well as from the supporting surface. As a result, the supporting surfaces are offset from the plane of the base area whereby, in the upper recording plate, they are downwardly offset and, in the lower recording plate, they are upwardly offset. The supporting surfaces are upwardly angled with regard to the base area of the respective recording plate at approximately the same angle. Corner areas (124, 125; 224, 225) of the supporting surfaces located outside and at the rear are approximately shaped in the form of an isosceles right triangle and are upwardly angled.

20 Claims, 2 Drawing Sheets

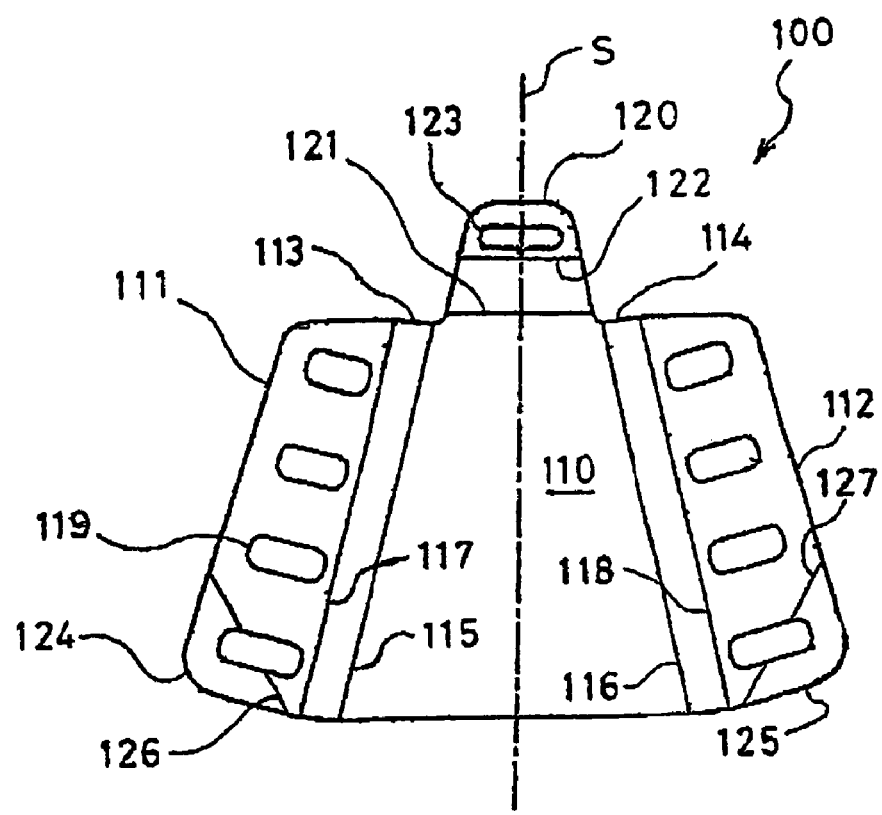
Fig. 1a
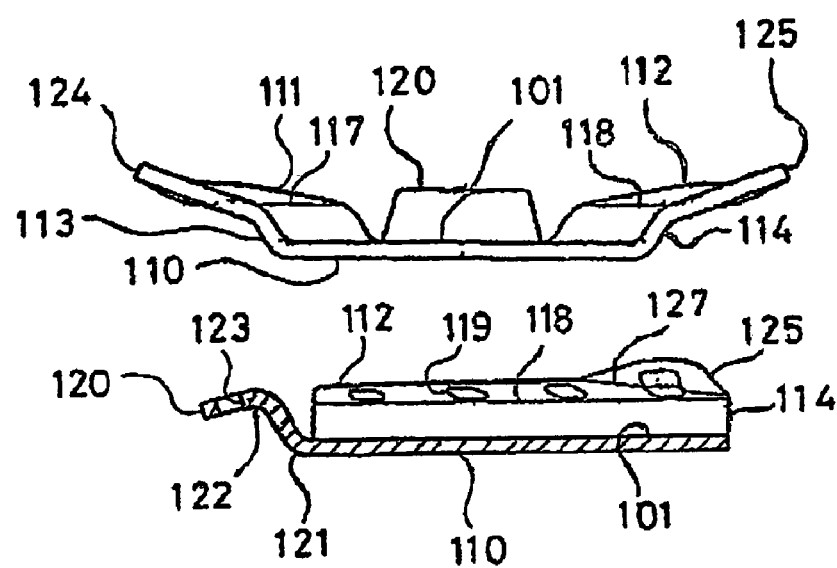
Fig. 1b
Fig. 1c

DENTAL DEVICE FOR RECORDING THE POSITION OF THE JAWS OF A PATIENT IN RELATION TO ONE ANOTHER BY MEANS OF RECORDING PLATES

This application claims priority of PCT application PCT/CH2004/000073 having a priority date of Mar. 18, 2003 the disclosure of which is hereby incorporated herein by reference.

TECHNICAL FIELD

The present invention relates to a dental device for recording the position of the jaws of a patient in relation to one another, the device comprising a pair of recording plates, of which at least one is in one piece and has a substantially planar extent with almost constant thickness, an upper recording plate being able to be secured on the upper jaw of the patient, and a lower recording plate being able to be secured on the lower jaw of the patient, each of the recording plates being mirror-symmetric about a sagittal plane relative to the position of a pair of recording plates fitted in situ in the patient, and one recording plate being provided with a plane writing surface and the other recording plate being provided with a stylus which is designed to cooperate with the writing surface.

BACKGROUND OF THE INVENTION

Recording devices of the type mentioned above are known in the dental field. Their recording plates have to be fixed on the natural or prosthetic teeth of the patient to ensure that they do not slip and that the tongue does not push them aside. After the recording plates have each been secured on the upper jaw and lower jaw, respectively, of the patient (for example with rapidly setting dental silicone), the patient is asked to bite, i.e. to press the jaws together, and also the recording plates fitted on them, whereupon the stylus is pressed onto the opposite writing surface. The patient is then asked to make certain movements of the lower jaw relative to the upper jaw, whereupon the stylus draws a tracing on the writing surface, for example by leaving a scratch mark in a wax layer applied to the writing surface. From this tracing, or so-called "arrow point", a skilled person, for example a dentist, is able to derive information concerning the position of the patient's jaws in relation to one another, for example for production of a removable or permanent dental prosthesis or for monitoring the occlusion of the existing teeth of the patient.

In the recording device, the stylus can be arranged on the upper recording plate or on the lower recording plate, both arrangements having their advantages and disadvantages. If the stylus is arranged on the upper recording plate, the tracing is more easily and more conveniently visible to the skilled person, even though the wrong way round, and thus easier to view, but consequently more difficult to interpret. In the converse scenario, the tracing is less easily and less conveniently visible, but the right way round, and thus more difficult to view but easier to interpret.

To be able to be used correctly in dentistry, the recording device, when placed in the patient's mouth, must force the pressed-together jaws of the patient forwardly (in specialist terminology "anteriorly") at the center by not more than about a centimeter and must prevent the normal bite position (in specialist terminology "occlusion") from being reached. A main reason for this is that, in the case of fairly wide opening, the nature of the jaw joint not only effects a pure rotation (in which the jaw compass opens) but also an undesired sagittal movement (in which the lower jaw moves forward). Therefore, there is not much available height for the construction of the recording device, and for this reason the previously known recording devices, except for newly produced total prostheses, are cumbersome and their recording plates are difficult to secure on the jaws of the patient. In other words, working with them involves considerable effort and time. In the prior art, there are no recording plates available that can be used for all dental situations or at least for the majority of them. In the case of dentulous patients in particular, the skilled person has to spend more time in producing upper and lower plastic plates, because the recording plates have to be integrated into a plastic base adapted exactly to the teeth. The corresponding time spent doing this increases the cost to the patient (and if appropriate to the health insurance companies).

U.S. Pat. No. 2,481,203 discloses a device for recording the position of two mastication surfaces in relation to one another. The recording plates appear to be configured in such a way that they can be guided on the dentition; in reality, however, no guiding is guaranteed in the vertical direction. This is because the recording plates have a dish-shaped base so that no space is lost in the vertical direction and so that the supporting pin has vertical space therein. There is admittedly also a lateral abutment on the dentition as soon as suitable compounds (for example of silicone) are placed between the recording plates and the teeth. By contrast, however, vertical support is obtained only on the mucosa, not on the dentition.

This device and other known devices do not permit reliable recording of dentulous patients without preliminary work being carried out, for example individual production of suitable plastic parts. In the case of dentulous patients, reliable recording without the need for preliminary work is as yet an unsolved problem.

SUMMARY OF THE INVENTION

Accordingly, the object of the invention is to propose a device of the type mentioned in the introduction which, compared to the prior art, is less awkward to use, in particular easier and thus quicker. No complex preparatory work should be needed in the laboratory and dental clinic, and the recording plates stocked in various sizes should be able to be used for all dental situations that arise or at least for the majority of these situations. In particular, however, handling is intended to be improved considerably by the fact that both lateral guiding and also vertical guiding of the recording plate are obtained and, if appropriate, also forward guiding of the recording plate on the dentition without special measures being needed to this end.

In a device of the type mentioned in the introduction, this object is achieved by the combination of features defined in claim 1. Advantageous embodiments of the invention are defined in the dependent claims.

An advantage of the invention thus defined is in particular that upper and lower recording plates can be produced and kept in stock in different sizes, so that, for every situation arising (patient with full set of teeth, partial set of teeth, no teeth or with dentures), a suitably selected upper recording plate and lower recording plate can be found and used, essentially without any preparatory work.

A further advantage of the invention thus defined is that the recording plates have wing-like support surfaces with which, in the case of dentulous patients and patients with dentures, they lie on the tooth surfaces, or, in the case of edentulous patients, on wax templates. In each recording plate, therefore, the particular angling of the support surfaces in relation to the base area, and of the corner areas in relation to the rest of the support surface, gives the recording plate a spatial shape which is generally well adapted to the dentition and its spatial curvature (both transverse and sagittal), and, in particular, the bearing contact of the wing-like support surfaces, in combination with the depression of the middle part of one or both recording plates, permits direct support on the teeth together with lateral securing against displacement and, consequently, reliable recording of dentulous patients without any preparatory work.

An advantage of the narrowing of the support surfaces of the recording plates, and in particular of the pronounced narrowing of the support surfaces of the upper recording plate toward the front, relative to the position of the recording plates fitted in situ in the patient, is that, by virtue of this measure, the premolars do not impede the fitting of the recording plates, and the room for maneuver during fitting of the recording plates is slightly greater.

An advantage of the interaction of the dual angling of the support surfaces—in relation to the base area and in relation to the respectively adjacent transition area—and of the resulting offset arrangement of the support surfaces from the plane of the base area is that, relative to the position of the recording plates fitted in situ in the patient, the transition areas act as shoulders or steps which stabilize the position of the recording plate transversely in the plane of the base area, while the forwardly narrowing trapezoid shape of the base area helps to position the recording plate sagittally in the plane of the base area.

By virtue of the continuous retention openings arranged on them, the support surfaces can be easily and quickly secured on the tooth surfaces or on the wax templates by means of dental silicone. In the case of real tooth surfaces, the dental silicone is injected directly in the presence of the patient under the support surfaces of the recording plate, and the support surfaces of the recording plate provided with dental silicone are then pressed onto the rows of teeth or wax rims. Since the dental silicone sets rapidly, the skilled person, after testing the position of the recording plates, is able to begin the recording operation immediately, i.e. without an additional treatment session and after just a short time (a few minutes). In the case of existing dentures, the support surfaces can be fixed in the same way as in the case of real tooth surfaces. In the case of wax templates, the support surfaces can be melted as usual onto the wax template and/or fixed with wax. Thus, the invention eliminates the preparatory laboratory work required in the prior art, and the patient is saved the need for at least one preparatory treatment session, and thus spared the corresponding inconvenience.

BRIEF DESCRIPTION OF THE DRAWINGS

Illustrative embodiments of the invention are described in greater detail below with reference to the drawings in which identical parts are designated by the same reference labels in all the figures. In the drawings:

FIG. 1a shows an embodiment of a lower recording plate according to the invention, in a view from above in relation to the orientation of a patient on whose lower jaw the recording plate is arranged;

FIG. 1b shows the same embodiment of the lower recording plate according to the invention as in FIG. 1a, in a view from behind in relation to the orientation of a patient on whose lower jaw the recording plate is arranged;

FIG. 1c shows the same embodiment of the lower recording plate according to the invention as in FIG. 1a, in a sagittal cross-sectional view from the left in relation to the orientation of a patient on whose lower jaw the recording plate is arranged.

DETAILED DESCRIPTION OF THE INVENTION

In the following text, indications such as above/below, inside/outside, front/behind, horizontal/vertical, transverse/sagittal and the like always relate to the orientation of the patient on whose jaw a recording plate according to the invention is arranged.

The dental device according to the invention for recording the position of the jaws of a patient in relation to one another comprises a pair of recording plates 100 and 200, of which an upper recording plate is intended to be secured on the upper jaw of the patient, and a lower recording plate is intended to be secured on the lower jaw of the patient.

Figure 2A:
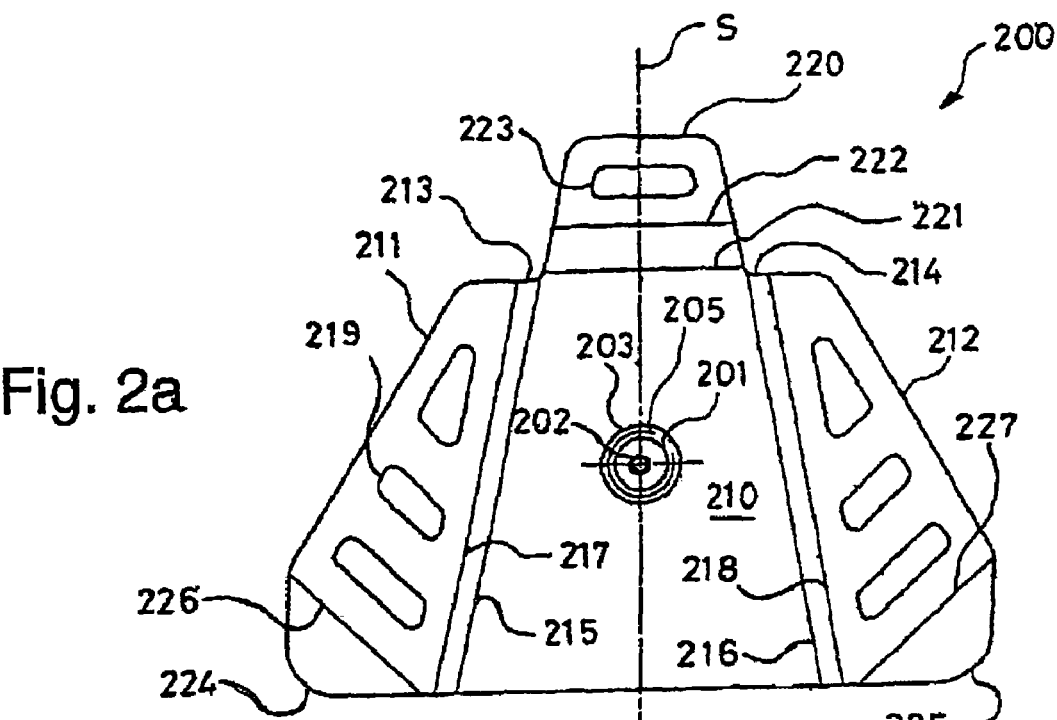
FIG. 2a shows an embodiment of an upper recording plate according to the invention with inserted pin and stylus, in a view from below in relation to the orientation of a patient on whose upper jaw the recording plate is arranged.
Figure 2B:
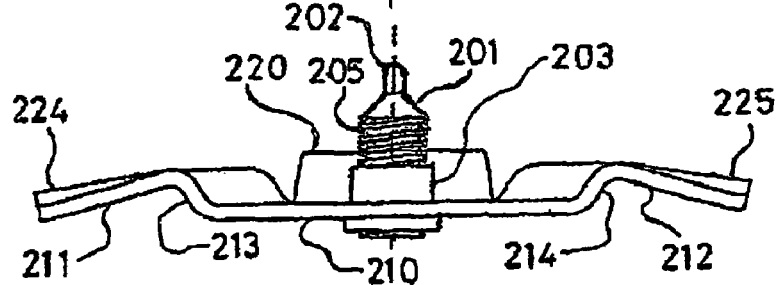
FIG. 2b shows the same embodiment of the upper recording plate according to the invention as in FIG. 2a, again with inserted pin and stylus, in a view from behind in relation to the orientation of a patient on whose upper jaw the recording plate is arranged.
Figure 2C:
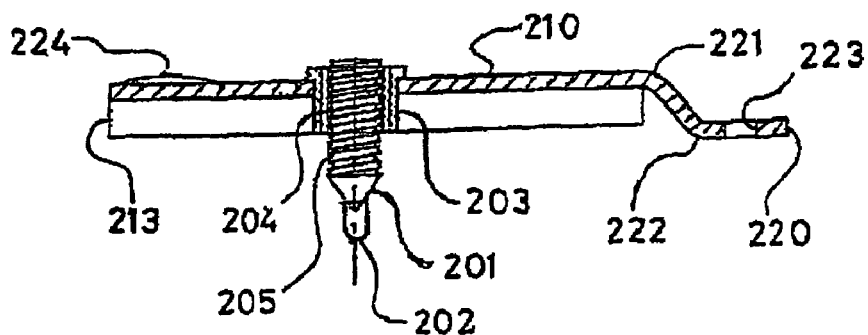
FIG. 2c shows the same embodiment of the upper recording plate according to the invention as in FIG. 2a, in a sagittal cross-sectional view of the recording plate from the right in relation to the orientation of a patient on whose upper jaw the recording plate is arranged, while the pin with stylus inserted in the recording plate is shown in a side view, i.e. not in cross section.

The embodiment of a lower recording plate 100 shown in FIGS. 1a, 1b and 1c and the embodiment of an upper recording plate 200 shown in FIGS. 2a, 2b and 2c are each mirror-symmetric about a sagittal plane S.

As will be seen from the figures, each recording plate has a substantially planar extent and almost constant thickness. If such recording plates are made of metal such as stainless steel, they can be produced by working a metal plate (pressing, punching, bending and the like), resulting in said planar extent and constant thickness. However, the use of other materials and production methods, for example plastic using pressing and/or injection molding, is not excluded.

To record the position of the jaws of a patient in relation to one another, the upper recording plate 200 in the illustrative embodiment shown is provided with a pin 201 with stylus 202, and the lower recording plate 100 is provided with a plane writing surface 101 for the stylus 202. To secure the pin 201 on the upper recording plate 200, a guide sleeve 203 is mounted substantially at the center of a plane base area 210 of the upper recording plate 200, for example punched into it. One end of the pin 201 is arranged and received in this guide sleeve 203, and the stylus 202 is formed at the other, free end of the pin 201. In the illustrative embodiment shown, the guide sleeve 203 is secured on the upper recording plate 200 by means of a press fit, and the guide sleeve 203 is provided with a continuous threaded bore 204 into which the pin 201 is screwed via an external thread 205 provided on said pin. Other fixing means are, however, also conceivable. For example, the guide sleeve could be welded on in the base area of the recording plate, and the pin could, for example, be secured in the guide sleeve by means of a screw let into the guide sleeve or by clamping of the guide sleeve, and the pin could also be produced in one piece with the recording plate, for example directly punched out from the latter.

A wax layer can be applied to a plane base area 110 of the lower recording plate 100, or a film sensitive to writing pressure can be affixed thereto, so that the stylus 202, when applied to the writing surface 101 thus prepared, interacts with it and leaves a tracing thereon, or on the wax layer or film, upon each relative movement, and from this tracing it is possible, as has already been mentioned, to derive information concerning the position of the jaws of the patient in relation to one another.

Apart from the guide sleeve 203 and the pin 201 attached therein, which are not to be understood as components of the upper recording plate 200 but as writing tools attached thereto, each of the two recording plates 100 and 200 is in each case made as a single part.

Each of the two recording plates 100 and 200 comprises a pair of support surfaces 111, 112 and 211, 212, respectively, which are arranged on both sides of their plane base area 110 and 210, respectively, and of the sagittal plane S and are mirror-symmetric about this sagittal plane S, and also a pair of substantially plane transition areas 113, 114 and 213, 214, respectively, which are arranged adjacent to the respective base area 110 and 210 and adjacent to one of the support surfaces 111, 112 and 211, 212, respectively and are mirror-symmetric about the sagittal plane S. Each transition area 113, 114 and 213, 214, respectively, is angled away both from the adjacent base area 110 and 210, respectively, and also from the adjacent support surface 111, 112 and 211, 212, respectively, in such a way that, as a result of the sequence of these two angled formations, the support surfaces are offset from the plane of the base area. The respective angled formations, in relation to the position of a recording plate fitted in situ in the patient, are oriented such that the offset of the support surfaces from the plane of the base area is downward in an upper recording plate 200 and upward in a lower recording plate 100, as shown in FIGS. 1c and 1c and FIGS. 2b and 2c, respectively.

For adaptation to the shape of the patient's jaws, the respective base area 110, 210 has almost the shape of an isosceles trapezoid which narrows in a delta formation toward the front and is mirror-symmetric about the sagittal plane S, which helps to position the relevant recording plate sagitally in the plane of its base area, i.e. substantially horizontal in the patient's mouth. Furthermore, to permit adaptation to the shape of the patient's jaws and in addition to provide the aforementioned angled formations and aforementioned offset of the support surfaces 111, 112 and 211, 212 from the plane of the respective base area 110 and 210, respectively, each transition area 113, 114 and 213, 214 is elongate and almost parallelogram-shaped, as can be seen in particular from FIG. 1a and FIG. 2a, respectively. Each transition area 113, 114 and 213, 214 bears with one of its longer sides 115, 116 and 215, 216, respectively, on one of the nonparallel sides of the almost trapezoid base area 110, 210 and with the other of its longer sides 117, 118 and 217, 218, respectively, on one of the support surfaces 111, 112 and 211, 212, respectively.

For the best possible adaptation of the position of the support surfaces 111, 112 and 211, 212, respectively, to the position of the tooth surfaces or wax templates on which the support surfaces are to be secured, the support surfaces 111, 112 and 211, 212 of the upper and lower recording plates 100, 200, respectively, are angled upwardly in relation to the base area 110, 210 of the respective recording plate at approximately the same angle. In addition, each of the support surfaces 111, 112 and 211, 212 has a corner area 124, 125 and 224, 225, respectively, which is located outside and at the rear and which is almost in the form of an isosceles right-angled triangle, with a hypotenuse 126, 127 and 226, 227, respectively, of said triangle adjoining the rest of the support surface, and angled upwardly in relation to the rest of the support surface. Thus, the corner area in question is angled upwardly relative to the base area of its recording plate even more than the rest of the support surface of this recording plate, as can be seen in particular from FIGS. 1b and 1c and FIGS. 2b and 2c, respectively. In the upper and lower recording plates 100 and 200, the corner areas 124, 125 and 224, 225, respectively, are angled upwardly relative to the rest of the support surface of the respective recording plate by approximately the same angle, as is also the case for the support surfaces relative to the base area of the respective recording plate, with the result that the protruding corner areas formed on the support surfaces do not prevent the upper and lower support surfaces from fitting one another.

Another contribution to ensuring the best possible adaptation of the support surfaces 111, 112 and 211, 212 to the position of the tooth surfaces or wax templates, on which the support surfaces are to be secured, is afforded by the shape of the support surfaces. As can be seen from FIG. 1a, the support surfaces 111, 112 of the lower recording plate 100 are almost trapezoid, both when seen including and also excluding the respective corner area 124, 125, this trapezoid shape differing little from a rectangular shape because the support surfaces 111, 112 of the lower recording plate 100 narrow toward the front by not more than a dozen angle degrees, preferably by approximately 6°. As can be seen from FIG. 2a, the support surfaces 211, 212 of the upper recording plate 200 are substantially pentagonal but once again, when excluding the respective corner area 224, 225, are almost trapezoid, this trapezoid shape differing little from a triangular shape because the support surfaces 211, 212 of the upper recording plate 200 narrow toward the front in a pronounced delta shape.

Each of the support surfaces 111, 112 and 211, 212 is provided with several continuous retention openings 119 and 219, respectively, which, as has already been mentioned, serve to secure the support surfaces on tooth surfaces or wax templates by means of dental silicone. With regard to this securing effect, an advantageous compromise for the relative dimensions of support surface and retention openings is one in which the cumulative dimension of the retention openings 119, 219 on the support surface represents up to a third of the dimension of the total support surface 111, 112 and 211, 212, respectively.

To make them easier to handle, the recording plates 100 and 200 are provided, centrally toward the front (in specialist terminology "anteriorly") and adjacent to their respective base area 110 and 210, with a respective extension piece 120 and 220 which is mainly intended to serve as a grip for the operator's fingers or for forceps. For this purpose, the extension piece 120 and 220, in the same way as the support surfaces 111, 112 and 211, 212, is offset from the plane of the base area by a sequence of two angled formations at respective bend points 121, 122 and 221, 222, respectively, and is additionally provided with a through-opening 123 and 223, respectively, in the area of its free end. The angled formations of the extension pieces 120 and 220 are dimensioned in such a way that the free end of the extension piece 220 of the upper recording plate 200 extends forward almost horizontally, i.e. parallel to the base area 210 (FIG. 2c), whereas the free end of the extension piece 120 of the lower recording plate 100 extends downward toward the front, i.e. obliquely with respect to the plane of the base area 110 (FIG. 1c).

LIST OF REFERENCE LABELS

S sagittal plane
100 lower recording plate
101 writing surface
110 base area of lower recording plate 100
111 support surface of lower recording plate 100
112 support surface of lower recording plate 100
113 transition area between support surface 111 and base area 110
114 transition area between support surface 112 and base area 110
115 longer side of transition area 113
116 longer side of transition area 114
117 longer side of transition area 113
118 longer side of transition area 114
119 retention openings on support surfaces 111, 112
120 extension piece on base area 110 of lower recording plate 100
121 angling of extension piece 120
122 angling of extension piece 120
123 opening in extension piece 120
124 corner area
125 corner area
126 hypotenuse of corner area 124
127 hypotenuse of corner area 125
200 upper recording plate
201 pin
202 stylus
203 guide sleeve
204 threaded bore of guide sleeve 203
205 external thread of pin 201
210 base area of upper recording plate 200
211 support surface of upper recording plate 200
212 support surface of upper recording plate 200
213 transition area between support surface 211 and base area 210
214 transition area between support surface 212 and base area 210
215 longer side of transition area 213
216 longer side of transition area 214
217 longer side of transition area 213
218 longer side of transition area 214
219 retention openings on support surfaces 211, 212
220 extension piece on base area 210 of upper recording plate 200
221 angling of extension piece 220
222 angling of extension piece 220
223 opening in extension piece 220
224 corner area of support surface 211
225 corner area of support surface 212
226 hypotenuse of corner area 224
227 hypotenuse of corner area 225

The invention claimed is:

1. A dental device for recording the position of the jaws of a patient in relation to one another, the device comprising a pair of recording plates, said pair of recording plates comprising an upper recording plate and a lower recording plate, at least one of said recording plates being in one piece and having a substantially planar extent with almost constant thickness, the upper recording plate being able to be secured on the upper jaw of the patient, and the lower recording plate being able to be secured on the lower jaw of the patient, each of the recording plates being mirror-symmetric about a sagittal plane relative to the position of the pair of recording plates when fitted in situ in the patient, and one recording plate being provided with a plane writing surface and the other recording plate being provided with a stylus which is designed to cooperate with the writing surface, wherein said recording plates have a planar base area, a pair of support surfaces on both sides of the planar base area and of the sagittal plane, with piercing retention openings arranged on said support surfaces, and a pair of substantially planar transition areas arranged adjacent to the base area and to a respective support surface, the base area having almost the shape of an isosceles trapezoid which tapers in a delta formation toward the front and is mirror-symmetric about the sagittal plane, whereas each transition area is elongate and approximately parallelogram-shaped and bears with one of its longer sides on one of the nonparallel sides of the almost trapezoid base area and with the other of its longer sides on one of the support surfaces, and each transition area being angled away both from the adjacent base area and also from the adjacent support surface in such a way that the support surfaces are offset from the plane of the base area, specifically, downwardly offset in the upper recording plate and upwardly offset in the lower recording plate relative to the position of said pair of recording plates when fitted in situ in the patient.

2. The device as claimed in claim 1, wherein relative to the position of the pair of recording plates when fitted in situ in the patient, the support surfaces of the upper and lower recording plates are angled upwardly in relation to the corresponding base area of the respective recording plate at approximately the same angle.

3. The device as claimed in claim 2, wherein each support surface has an approximately quadrilateral shape and comprises a corner area and a main portion excluding the respective corner area, said corner area being located exterior and posterior relative to the position of the pair of recording plates when fitted in situ in the patient. said corner area being approximately in the form of an isosceles right-angled triangle with a hypotenuse of said triangle adjoining the main portion of the support surface, and said corner area being angled upwardly at said hypotenuse in relation to the main portion of the support surface and thus being angled upwardly relative to the base area of the respective recording plate even more than the main portion of the support surface.

4. The device as claimed in claim 3, wherein relative to the position of the pair of recording plates when fitted in situ in the patient, the corner areas of the support surfaces of the upper and lower recording plates are in each case angled at approximately the same angle in relation to the remainder of the support surface of the respective recording plate.

5. The device as claimed in claim 4 wherein at least one of the support surfaces has several piercing retention openings extending through the recording plate, and a cumulative cross-sectional area of the retention openings on the support surface represents up to a third of an area of the total support surface.

6. The device as claimed in claim 3 wherein at least one of the support surfaces has several piercing retention openings extending through the recording plate, and a cumulative cross-sectional area of the retention openings on the support surface represents up to a third of an area of the total support surface.

7. The device as claimed in claim 3 wherein the support surfaces of the lower recording plate, whether including or excluding the respective corner area, are approximately trapezoid, and, relative to the position of the lower recording plate when fitted in situ in the patient, they taper toward the front by not more than a dozen angle degrees.

8. The device as claimed in claim 7, wherein the support surfaces of the lower recording plate taper toward the front by approximately 6° relative to the position of the lower recording plate when fitted in situ in the patient.

9. The device as claimed in claim 3 wherein the support surfaces of the upper recording plate are substantially pentagonal and, excluding the respective corner area, are substantially trapezoid and appear approximately triangular, since they taper to a considerable extent toward the front relative to the position of the upper recording plate fitted in situ in the patient.

10. The device as claimed in claim 2 wherein at least one of the support surfaces has several piercing retention openings extending through the recording plate, and a cumulative cross-sectional area of the retention openings on the support surface represents up to a third of an area of the total support surface.

11. The device as claimed in claim 2 wherein the support surfaces of the lower recording plate, whether including or excluding the respective corner area, are approximately trapezoid, and, relative to the position of the lower recording plate when in situ in the patient, they taper toward the front by not more than a dozen angle degrees.

12. The device as claimed in claim 11, wherein the support surfaces of the lower recording plate taper toward the front by approximately 6° relative to the position of the lower recording plate when fitted in situ in the patient.

13. The device as claimed in claim 2 wherein the support surfaces of the upper recording plate are substantially pentagonal and, excluding the respective corner area, are substantially trapezoid and appear approximately triangular, since they taper to a considerable extent toward the front relative to the position of the upper recording plate fitted in situ in the patient.

14. The device as claimed in claim 1 wherein at least one of the support surfaces has several piercing retention openings extending through the recording plate, and a cumulative cross-sectional area of the piercing retention openings on the support surface represents up to a third of an area of the total support surface.

15. The device as claimed in claim 14 wherein the support surfaces of the lower recording plate, whether including or excluding the respective corner area, are approximately trapezoid, and, relative to the position of the lower recording plate when fitted in situ in the patient, they taper toward the front by not more than a dozen angle degrees.

16. The device as claimed in claim 15, wherein the support surfaces of the lower recording plate taper toward the front by approximately 6° relative to the position of the lower recording plate when fitted in situ in the patient.

17. The device as claimed in claim 14 wherein the support surfaces of the upper recording plate are substantially pentagonal and, excluding the respective corner area, are substantially trapezoid and appear approximately triangular, since they taper to a considerable extent toward the front relative to the position of the upper recording plate fitted in situ in the patient.

18. The device as claimed in claim 1 wherein the support surfaces of the lower recording plate, whether including or excluding the respective corner area, are approximately trapezoid, and, relative to the position of the lower recording plate fitted in situ in the patient, they taper toward the front by not more than a dozen angle degrees.

19. The device as claimed in claim 18, wherein the support surfaces of the lower recording plate taper toward the front by approximately 6° relative to the position of the lower recording plate when fitted in situ in the patient.

20. The device as claimed in claim 1 wherein the support surfaces of the upper recording plate are substantially pentagonal and, excluding the respective corner area, are substantially trapezoid and appear approximately triangular, since they taper to a considerable extent toward the front relative to the position of the upper recording plate fitted in situ in the patient.

* * * * *